United States Patent [19]

Insley

[11] Patent Number: 4,813,948
[45] Date of Patent: Mar. 21, 1989

[54] MICROWEBS AND NONWOVEN MATERIALS CONTAINING MICROWEBS

[75] Inventor: Thomas I. Insley, St. Paul, Minn.

[73] Assignee: Minnesota Mining and Manufacturing Company, St. Paul, Minn.

[21] Appl. No.: 91,730

[22] Filed: Sep. 1, 1987

[51] Int. Cl.[4] .............................................. A61F 13/16
[52] U.S. Cl. ..................................... 604/366; 428/92;
428/221; 428/224; 428/283; 428/284; 428/297;
428/298; 428/326; 428/364; 428/372; 428/903;
428/913; 428/288; 604/358
[58] Field of Search ................. 428/92, 221, 224, 284,
428/283, 326, 297, 298, 288, 364, 372, 903, 913;
604/358, 366, 367, 370

[56] References Cited

U.S. PATENT DOCUMENTS

| | | | |
|---|---|---|---|
| 2,988,782 | 6/1961 | Parrish et al. | 18/48 |
| 3,016,599 | 1/1962 | Perry | 28/78 |
| 3,073,735 | 1/1963 | Till et al. | 156/38 |
| 3,316,904 | 7/1961 | Wall et al. | 128/146.6 |
| 3,892,909 | 7/1975 | Miller | 428/371 |
| 3,901,236 | 8/1975 | Assarsson et al. | 128/284 |
| 3,971,373 | 7/1976 | Braun | 128/146.2 |
| 4,011,067 | 3/1977 | Carey, Jr. | 55/354 |
| 4,065,599 | 12/1977 | Nishiumi et al. | 428/402 |
| 4,100,324 | 7/1978 | Anderson et al. | 428/299 |
| 4,103,062 | 7/1978 | Aberson et al. | 428/283 |
| 4,118,531 | 10/1978 | Hauser | 428/224 |
| 4,144,294 | 3/1979 | Werthaiser et al. | 264/15 |
| 4,239,043 | 12/1980 | Gellert | 128/285 |
| 4,259,400 | 3/1981 | Bolliand | 428/288 |
| 4,333,976 | 6/1982 | Okamoto et al. | 428/85 |
| 4,392,903 | 7/1983 | Endo et al. | 156/167 |
| 4,418,103 | 11/1983 | Tani et al. | 428/4 |
| 4,426,417 | 1/1984 | Meitner et al. | 428/195 |
| 4,429,001 | 1/1984 | Kolpin et al. | 428/283 |
| 4,469,734 | 9/1984 | Minto et al. | 428/134 |
| 4,588,635 | 5/1986 | Donovan | 428/288 |
| 4,604,313 | 8/1986 | McFarland et al. | 428/172 |
| 4,618,531 | 10/1986 | Marcus | 428/283 |
| 4,650,479 | 3/1987 | Insley | 604/358 |
| 4,666,763 | 5/1987 | Wong et al. | 428/221 |
| 4,681,789 | 7/1987 | Donovan et al. | 428/85 |

FOREIGN PATENT DOCUMENTS

0156649 10/1986 European Pat. Off. .

OTHER PUBLICATIONS

Feltham, F. J., "The Hansen Filter", Filtration & Separation, vol. 16, No. 4, Jul./Aug. 1979, pp. 370-372.
Polysteen-Superabsorbent-Fibre-Flock—Hanfspinnerei Steen & Co. GmbH.

Primary Examiner—James J. Bell
Attorney, Agent, or Firm—D. M. Sell; W. N. Kirn; C. Truesdale

[57] ABSTRACT

Microfiber microwebs are provided. The microfiber microwebs have relatively dense nuclei with individual fibers and/or fiber bundles protruding therefrom. The microfiber microwebs can be incorporated into nonwoven webs of blown microfibers, air-laid staple fibers, or wood pulp fibers as well as into shaped articles having porous covering materials. The microfiber microwebs are useful in sorbent, filtration, and thermal insulation materials. The microfiber microwebs are prepared by divellicating a microfiber web to form discrete particles of microfiber microwebs.

23 Claims, 3 Drawing Sheets

MICROWEBS AND NONWOVEN MATERIALS CONTAINING MICROWEBS

FIELD OF THE INVENTION

This invention relates to nonwoven materials particularly nonwoven materials which are useful as sorbent materials, filtration media, and thermal insulation. More particularly the invention relates to webs that comprise microwebs such as melt blown microfiber prepared as described in Wente, Van A., "Superfine Thermoplastic Fibers," *Industrial Engineering Chemistry*, vol. 48, pp. 1342-1346 and in Wente, Van A. et al., "Manufacture of Superfine Organic Fibers" Report No. 4364 of the Naval Research Laboratories, published May 25, 1954.

BACKGROUND OF THE INVENTION

Increased sorbency of fibrous nonwoven webs has been desired, particularly when the webs are for use in such products as disposable diapers, incontinent devices, surgical dressings, and wipers.

U.S. Pat. No. 4,100,324 (Anderson et al.) discloses a nonwoven fabric-like material which consists essentially of an air-formed matrix of thermoplastic polymer microfibers having an average fiber diameter of less than about 10 microns, and a multiplicity of individualized wood pulp fibers disposed throughout the matrix of microfibers and engaging at least some of the microfibers to space the microfibers apart from each other. The wood pulp fibers are interconnected by and held captive within the matrix of microfibers by mechanical entanglement of the microfibers with the wood pulp fibers.

U.S. Pat. No. 4,429,001 (Kolpin et al.) discloses sorbent sheet products which comprise a coherent web of entangled blown fibers and an array of solid high-sorbency liquid-sorbent polymeric particles dispersed within the web. The blown fibers are prepared by extruding liquid fiber-forming material into a high-velocity gaseous stream were the extruded material is attenuated and drawn into fibers. The sorbent particles are introduced into the stream of fibers and the mixture of fibers and particles is collected as an entangled coherent mass.

U.S. Pat. No. 4,650,479 (Insley) discloses a sorbent sheet product, particularly useful for disposable diapers, incontinent devices, and sanitary napkins, which comprises a coherent fibrous web that includes entangled blown polymeric fibers and high sorbency, liquid sorbent fibers intermingled with the blown polymeric fibers. The product may also contain liquid transport fibers.

European Patent Publication No. 0 156 649 (Minnesota Mining and Manufacturing Company) discloses a sorbent sheet product which comprises a coherent fibrous web that includes entangled blown fibers and liquid transport fibers intermingled with the blown fibers and an array of solid high sorbency liquid-sorbent polymeric particles uniformly dispersed and physically held within the web. The particles swell upon sorption of liquid, and the transport fibers cause increased and more rapid sorption of liquid by conducting the liquid from external portions of the web to internal portions of the web.

Increased efficiency of fibrous nonwoven webs used as filtration media, such as in face masks, cartridge filters, and other air filters, and liquid-liquid filters has been desired.

U.S. Pat. No. 3,073,735 (Till et al.) discloses a method for producing filters wherein fibers from a plurality of fiber-forming means are suspended in a gas stream and deposited on a collecting surface. The fibers of each fiber-forming means differ in physical characteristics from those of the other means, e.g., one of the fibers may be preformed, such as staple textile fibers and the other fiber may be produced in situ by feeding a plastic fiber-forming composition from a reservoir to a spraying unit which comprises a spraying tube positioned in the center of a nozzle through which air is forced at a high velocity. The fibers are deposited on the collecting device in such intermingled relationship that there is a gradual gradation in fiber property along one dimension of the filter.

U.S. Pat. No. 3,316,904 (Wall et al.) discloses a filtering web for face masks which comprises a dimensionally stable, expanded lofty web of a blend of discontinuous, relatively coarse thermoplastic fibers and relatively fine thermostable fibers adhered to one another in a manner providing a lofty reticulated web while yet remaining dimensionally stable and resistant to matting and the web requires no inert filler fibers or the like in its formation.

U.S. Pat. No. 3,971,373 (Braun) discloses a self-supporting durable flexible conformable low-pressure-drop porous sheet product that contains a uniform three-dimensional arrangement of discrete solid particles. The sheet product comprises, in addition to the particles, a web of melt-blown microfibers in which the particles are uniformly dispersed. The particles are physically held in the web, even though there is only point contact between the microfibers and the particles, whereby the full surface of the particles is available for interaction with a medium to which the sheet product is exposed.

U.S. Pat. No. 4,011,067 (Carey, Jr.) discloses a filter medium which can remove a high percentage of fine particles from a gas stream and which comprises a base porous web, one or more lightweight non-self-supporting layers of microfibers collected and carried on the base porous web, and a top porous web.

Increased thermal insulating properties in fibrous nonwoven webs have been desired, particularly when the webs are for use in such products as outerwear, such as ski jackets, sleeping bags, and bedding, such as comforters.

U.S. Pat. No. 3,892,909 (Miller) discloses fibrous bodies simulating natural bird down which include larger circular bodies, or figures of revolution, and smaller feather bodies, the feathery bodies tending to fill the voids formed by the larger circular bodies. The fibrous bodies are preferably formed from synthetic fiber tow.

U.S. Pat. No. 4,118,531 (Hauser) discloses a thermal insulating material which is a web of blended microfibers and crimped bulking fibers which are randomly and thoroughly intermixed and intertangled with the microfibers. The crimped bulking fibers are generally introduced into a stream of blown microfibers prior to their collection. This web combines high thermal resistance per unit of thickness and moderate weight.

U.S. Pat. No. 4,144,294 (Werthaiser et al.) discloses a substitute for natural down comprising sheets of garneted polyester which are separated into a plurality of small pieces, each of which pieces is generally formed into a rounded body. Each of the rounded bodies includes a plurality of randomly oriented polyester fibers therein, and each of the rounded bodies provides a substantial resiliency to permanent deformation after the application of force to them.

U.S. Pat. No. 4,588,635 (Donovan) describes synthetic down thermal insulating materials which are batts of plied card-laps of a blend of 80 to 95 weight percent of spun and drawn, crimped, staple, synthetic polymeric microfibers having a diameter of from 3 to 12 microns and 5 to 20 weight percent of synthetic polymeric staple macrofibers having a diameter of from more than 12, up to 50 microns. Donovan describes this fiber blend as comparing favorably to down or mixtures of down with feathers as an insulator in that it will provide an equally efficient thermal barrier, be of equivalent density, possess similar compression properties, have improved wetting and drying characteristics, and have superior loft retention while wet. The fibers form these batts by physical entanglement of the fibers achieved during carding. An expanded discussion of these same materials can be found in Dent, Robin W. et al., DEVELOPMENT OF SYNTHETIC DOWN ALTERNATIVES, Technical Report Natick/TR-86/021L - Final Report, Phase 1.

SUMMARY OF THE INVENTION

The present invention provides microfiber microwebs. The microwebs are formed by divellicating, or tearing apart, a source microfiber web to form discrete microwebs of microfibers. Microfibers are thermoplastic fibers, generally having an average fiber diameter of less than about 10 microns. The microfiber microwebs have a relatively dense nucleus of microfibers with individual fibers and/or fiber bundles protruding therefrom. The relatively dense nuclei are more dense and have less void volume than the source microfiber web from which the microfiber microwebs are prepared. The nuclei preferably have an average diameter of about 0.05 to 4 mm, more preferably 0.2 to 2 mm, and the fibers and/or fiber bundles extend from the nuclei to provide an overall diameter of about 0.07 to 10 mm, more preferably about 0.1 to 5 mm.

The present invention further provides a nonwoven web comprising carrier fibers, i.e., blown fibers, preferably melt blown microfibers, air-laid staple fibers, or wood pulp fibers, and microfiber microwebs contained or dispersed among the carrier fibers. When the carrier fibers are melt blown microfibers, the nonwoven web may also contain staple fibers. These nonwoven webs of carrier fibers and microfiber microwebs are useful, for example, as sorbent materials, filtration devices, and as thermal insulation. When the web is to be used as a liquid-sorbent material, the microwebs can further comprise sorbent particulate material. Such webs are particularly useful in constructions such as disposable diapers, incontinent devices, catamenial devices and surgical dressings. When the web is to be used for filtration purposes, e.g., for filtration of selected gases from air rather than particulate matter, the webs preferably comprise blown fibers or air-laid staple fibers and microfiber microwebs and can also further comprise sorbent particulate material.

The present invention also provides shaped sorbent articles comprising a porous covering, preferably a nonwoven porous covering, preferably a nonwoven stretch fabric covering having contained therein microfiber microwebs of this invention. The covering may be of any desired size or shape, in such shapes as pillows, pouches, tubes, blocks, balls, and pyramids. The shaped sorbent article may be flexible. Such shaped sorbent articles are particularly useful for hazardous material containment and absorbency and as packing materials.

The present invention further provides a method for producing microfiber microwebs comprising forming a microfiber web and divellicating the microfiber web to form discrete microfiber microwebs. The microfiber web is preferably formed by melt blowing a thermoplastic fiber forming polymer. Sorbent particulate material may be deposited into the microfiber web during the forming of the web and a binder material may be applied to the web to tack the microfibers and sorbent particulate material together.

The present invention also provides a method for producing the nonwoven webs of the invention comprising melt blown microfibers and microfiber microwebs, comprising the steps of (a) forming a first web of melt blown microfibers;
(b) divellicating said first melt blown microfiber web to form microfiber microwebs;
(c) forming a primary air stream of melt blown carrier fibers;
(d) forming a secondary air stream of said microfiber microwebs;
(e) merging said primary and secondary air streams under turbulent conditions such that said microfiber microwebs are distributed throughout said melt blown carrier fibers of said primary air stream;
(f) forming a web of said melt blown carrier fibers and said microfiber microwebs; and
(g) collecting said web of said melt blown carrier fibers and said microfiber microwebs.

The present invention still further provides a method for producing the nonwoven webs of the invention comprising staple carrier fibers and microfiber microwebs, the method comprising the steps of (a) forming a web of melt blown microfibers;
(b) divellicating the web of melt blown microfibers to form microfiber microwebs;
(c) mixing said microfiber microwebs with staple fiber;
(d) forming a nonwoven web of said mixture; and
(e) collecting said nonwoven web.

The present invention still further provides a method for producing the nonwoven webs of the invention comprising wood pulp carrier fibers and microfiber microwebs, the method comprising the steps of (a) forming a web of melt blown microfibers;
(b) divellicating the web of melt blown microfibers to form microfiber microwebs;
(c) individualizing wood pulp fibers;
(d) providing said microfiber microwebs in a first gas stream;
(e) providing said individualized wood pulp fibers in a second gas stream;
(f) merging said first and second gas streams to mix said microfiber microwebs with said wood pulp;
(g) forming a nonwoven web of said mixture; and
(h) collecting said nonwoven web.

DETAILED DESCRIPTION OF THE INVENTION

The microfiber microwebs of the invention are prepared from source microfiber webs such as, for example, those disclosed in Wente, Van A., "Superfine Thermoplastic Fibers," Industrial Engineering Chemistry, vol. 48, pp. 1342-1346 and in Wente, Van A. et al., "Manufacture of Superfine Organic Fibers" Report No. 4364 of the Naval Research Laboratories, published May 25, 1954, or from microfiber webs containing particulate matter such as those disclosed, for example, in U.S. Pat. No. 3,971,373 (Braun), U.S. Pat. No 4,100,324 (Anderson et al.), and U.S. Pat. No. 4,429,001 (Kolpin et al.), which references are incorporated herein as exemplifying preparation of source microfiber webs.

Figure 1:
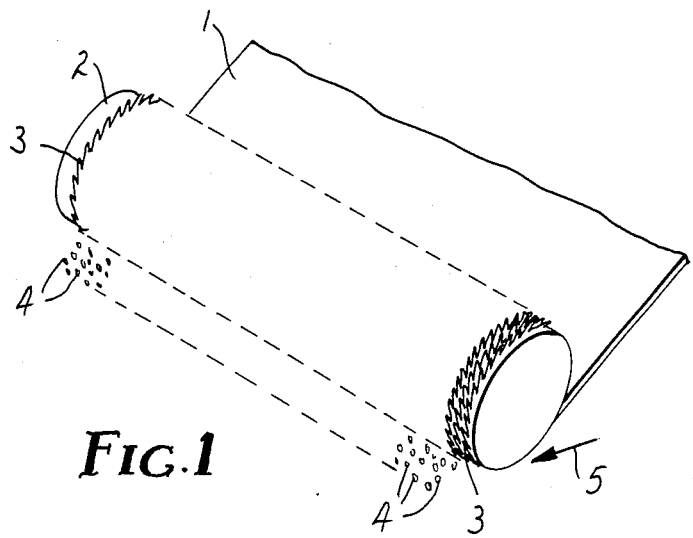
FIG. 1 is a perspective view of apparatus useful in the present invention.
Figure 2:
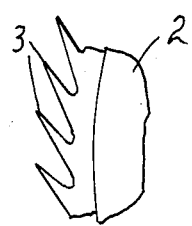
FIG. 2 is an enlarged side view of a tooth portion of the apparatus shown in FIG. 1.

The microfiber microwebs are prepared by mechanically divellicating, or tearing apart, the source microfiber web. Divellication can be accomplished, for example, by subjecting the source microfiber web to a lickerin as shown in FIG. 1. Source microfiber web 1 is fed to lickerin 2 which has, protruding from the surface thereof, teeth 3 which are further shown in perspective in FIG. 2. The teeth must be at a sufficiently low angle, e.g., preferably less than about 60°, more preferably less than about 40°, from the surface of the lickerin to produce the microwebs having a relatively dense nucleus with fibers and fiber bundles extending therefrom. The lickerin rotates, clockwise as depicted in FIG. 1, at a rate sufficient to divellicate source microfiber web 1 to form discrete microfiber microwebs 4. The source web is generally held in contact with the lickerin by means of a nose bar or delivery roll. Air stream 5 serves to remove microfiber microwebs 4 from the lickerin teeth. The microfiber microwebs can be collected for later incorporation into the nonwoven webs of the invention or the microfiber microwebs can be supplied directly from the lickerin into the carrier fiber stream.

The microfiber microwebs of the invention have a relatively dense nucleus with numerous individual fibers and/or fiber bundles extending therefrom. The extended fibers and fiber bundles provide an anchoring means for the microfiber microwebs when they are incorporated into a carrier matrix. In such a matrix, the carrier material, e.g., blown microfibers, staple fibers or wood pulp, can provide the principal, overall structural characteristics of the web, e.g., tensile properties and hand, thus permitting the microfiber microweb to be selected primarily for, e.g., sorbent or thermal properties rather than structural characteristics.

Figure 3:
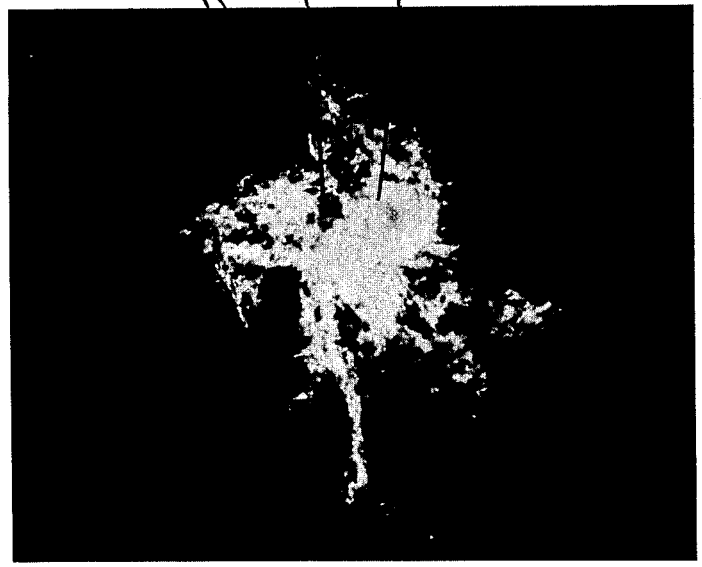
FIG. 3 is a photomicrograph of a microweb of the invention at 40X.

A typical microfiber microweb 4 is shown in FIG. 3 with nucleus 6 and fibers and fiber bundles 7 extending therefrom. The nucleus of the microfiber microwebs is preferably in the range of about 0.05 to 4 mm, more preferably about 0.2 to 2 mm. For example, the microfiber microweb of FIG. 3 has a nucleus which is about 0.5 mm in diameter and fibers and fiber bundles which extend from as little as 0.01 mm to as much as 0.4 and 0.6 mm. The extending fibers and/or fiber bundles preferably extend beyond the nucleus to provide an overall diameter of about 0.07 to 10 mm, more preferably about 0.1 to 5 mm.

The microfibers useful in forming the microfiber microwebs of the invention may be melt blown or they may be formed from solution when the microfiber source web is prepared without incorporated particulate material. When the microfiber source web is formed with incorporated particulate material, the microfibers are preferably melt blown. The melt blown microfibers of the microfiber microwebs may be formed from a wide variety of fiber-forming polymeric materials. Such polymeric materials include, for example, polyolefins, such as polypropylene and polyethylene, polyesters, such as polyethylene terephthalate, and polyamides, such as nylon 6 and nylon 66. Useful polymers for forming microfibers from solution include polyvinyl chloride, acrylics and acrylic copolymers, polystyrene, and polysulfone. Inorganic materials also form useful microfibers.

Figure 4:
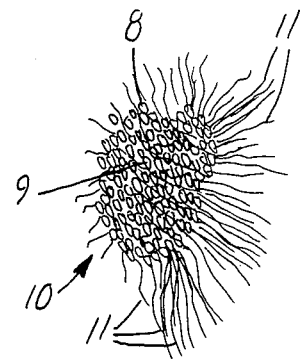
FIG. 4 is an enlarged view of a microweb of the invention containing sorbent particulate.

FIG. 4 is an enlarged view of a microfiber microweb containing particulate matter, such as results from divellication of a microfiber source web prepared according to Braun or Kolpin et al., supra, wherein particles 8 are predominantly entrapped within the nucleus 9 of microfiber microweb 10 by microfibers 11.

As can be seen from FIG. 3, the microfiber microweb is generally not round or ball-like, but rather has the extending fibers and fiber bundles directed away from the nucleus. The microfiber microweb generally has a portion of the nucleus from which few fibers or fiber bundles extend, e.g., in FIG. 3 that portion of the nucleus in the lower left portion of the photomicrograph. This configuration is believed to be due to the impact of the teeth of the lickerin roll and the dragging vector from the tearing action on the microfiber microwebs as they are being formed, with the top portion of the microfiber microweb in FIG. 1 being the portion on which a lickerin roll tooth impacted. For purposes of description herein, however, the microfiber microwebs will be described as if they were round with the maximum distance across the microfiber microweb being treated as the diameter.

The size and configuration of the microfiber microwebs is determined by the structure, i.e., density, component types, and amounts of components, of the microfiber source web and the size, density, and shape of the teeth on the divellicating device. The more dense the microfiber source web, the smaller the microfiber microweb and the shorter the trailing fibers and fiber bundles produced. The more brittle the microfibers in the microfiber source web, the smaller the microfiber microweb and the shorter the trailing fibers and fiber bundles produced. The smaller the diameter of the microfibers in the microfiber source web, the smaller the microfiber microweb and the longer the trailing fibers and fiber bundles produced. Larger teeth on the divellicating device produce larger microfiber microwebs with longer extending fibers and fiber bundles. Denser teeth on the divellicating device produce smaller microwebs with longer extending fibers and fiber bundles. Longer teeth on the divellicating device produce larger microwebs with longer extending fibers and fiber bundles.

Surprisingly, it has been found that microfiber source webs loaded with solid sorbent-type particulate materials can be divellicated to provide microfiber microwebs which include useful amounts of solid particulate material. The particulate-loaded microfiber microwebs possess the desirable properties of the microfiber source web on a small scale. However, advantageously, when the microfiber microwebs containing liquid-sorbent particulate material are incorporated into a nonwoven web, the flow of fluid through the web, e.g., from exterior portions to interior portions, is enhanced over the fluid flow through a web having the liquid-sorbent particulate incorporated directly into the web.

When the nonwoven web containing the microfiber microwebs is to be used for sorption of liquid, such as in disposable diapers, incontinent devices, or catamenial devices, the particulate material in the microfiber microwebs is a sorbent material such as wood pulp fiber or sorbent particulate. The preferred sorbent materials are generally super sorbent particles which rapidly sorb large quantities of liquids and retain the liquid under pressure. The more preferred sorbent particles for sorbing water are water-insoluble modified starches, such as, for example, those sorbent particulates described in U.S. Pat. No. 3,981,100 and high molecular weight acrylic polymers containing hydrophilic groups. A wide variety of commercially available water-insoluble, water-sorbing particles typically sorb 20 or more times their weight of water and preferably 100 or more times their weight of water. With such modified starches and acrylic polymers the amount of water sorbed generally decreases as impurities in the water, such as salts and ionic species, increase. Among sorbent particles useful for sorbing liquids other than water are alkylstyrene sorbent particles, such as Imbiber Beads ™, available from Dow Chemical Company. Such alkylstyrene sorbent articles generally sorb about 5 to 10 times or more their weight of liquid. In general, sorbent particles should sorb at least their weight of liquid.

When the nonwoven web containing the microfiber microwebs is to be used for air purification, i.e., sorption of vapors or contaminants from the air, the particulate material in the microfiber microwebs is a sorbent material of the type commonly used to remove the particular vapor or contaminant. Typical particles for use in filtering or purifying devices include activated carbon, alumina, sodium bicarbonate, and silver particles which remove a component from a fluid by adsorption, chemical reaction, or amalgamation or such particulate catalytic agents as hopcalite, which catalyze the conversion of a hazardous component, as well as clay and clay treated with acidic solutions, such as acetic acid, or alkaline solutions, such as aqueous sodium hydroxide.

The sorbent particles may vary in size from about 5 to 3000 micrometers in average diameter. Preferably the particles are less than about 1500 micrometers in average diameter. The maximum particle size useful in any particular microfiber microweb depends on both the size of the microfiber microweb and the effective fiber size of the microfibers in the microfiber microweb. Preferably, the particle size is about 5 times less than the diameter of the nucleus of the microfiber microweb, and typically 100 to 1000 micrometers in average diameter.

The amount of sorbent particles in the microfiber microweb depends on the particular use for which the nonwoven web containing the particulate-loaded microfiber microweb is to be used and the amount of microfiber microweb incorporated in the nonwoven web. Generally, the amount of sorbency desired must be balanced with other properties, such as the integrity, or strength, of the microfiber microweb as well as the size of the microfiber microweb. In the microfiber source web from which the microfiber microwebs are divellicated, sorbent particles generally comprise at least about 5 $g/m^2$ for each 100 $g/m^2$ of microfiber, preferably as much as 150 $g/m^2$ for each 100 $g/m^2$ microfiber, and in some applications as much as 500 $g/m^2$ or more for each 100 $g/m^2$ microfiber.

To achieve the higher loadings of sorbent particles in the microfiber microwebs, e.g., 500 $g/m^2$ or more of sorbent particles for each 100 $g/m^2$ microfiber, a binder material may be optionally added to the microfiber source web when the web is being formed, or may be applied to the source web after formation but before divellication, or may be applied to the microfiber microwebs after divellication. Generally, application of the binder material is more effective when the binder material is added during source web formation or applied to the source web prior to divellication. The binder material should be sufficiently sticky to tack the microfibers and particles together, but not so sticky as to bond the microweb structure itself. Preferably, the binder material is hydrophilic when the microfiber microweb is to be used for sorption of aqueous liquids. Such binder materials include glycerol, polyethylene glycol, polyols, and polyethers.

Alternatively, the sorbent particles can be incorporated into the melt blown microfiber matrix while the microfibers are still tacky to cause adhesion of the sorbent particulate to the microfibers.

The amount of binder material present should be sufficient to effect adhesion of the sorbent particles and microfibers, but not so great as to coat the particles and interfere with the sorbent properties of the particles. Generally, a small amount of binder material, e.g., about 0.5 to 2 percent by weight of the microfiber microweb, is sufficient to provide the additional cohesion desired to improve retention of the sorbent particles in the microfiber microweb when using sorbent particle loadings of 500 $g/m^2$ or more for 100 $g/m^2$ of microfiber.

Surfactants can be incorporated in the microwebs and/or nonwoven materials of the invention. The surfactants can be applied by aerosol to microwebs before or after their incorporation into a carrier. Surfactants can be incorporated by any suitable method into a source web before it is used to form microwebs. Surfactants can also be applied to product webs which include microwebs.

Figure 5:
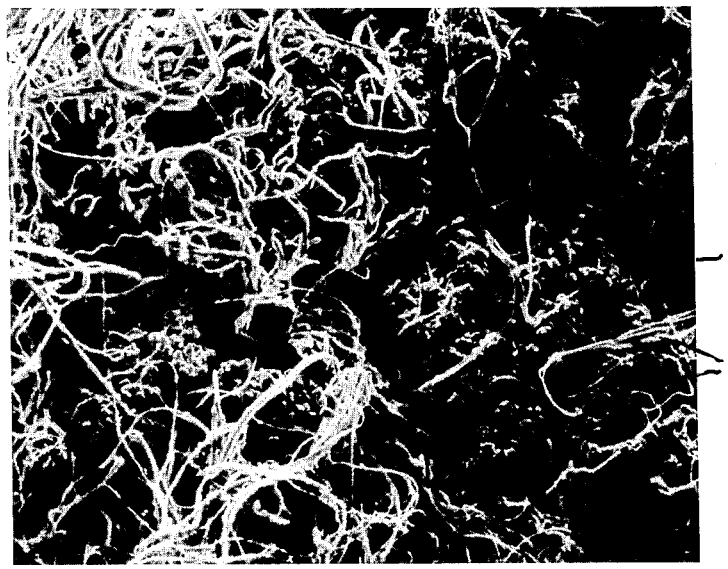
FIG. 5 is a photomicrograph of a nonwoven web of the invention comprising microwebs containing sorbent particulate in a carrier matrix of blown microfibers.
Figure 6:
FIG. 6 is a photomicrograph of a nonwoven web of the invention comprising microwebs and staple fiber at 40X.

The microfiber microwebs of the invention are particularly useful when incorporated in nonwoven webs. Such nonwoven webs include blown fiber webs, particularly melt blown microfiber webs, and air-laid staple fiber webs. FIG. 5 is a microphotograph of a blown microfiber web containing microfiber microwebs loaded with sorbent particulate 11. It can be noted that microfibers 12 of the microfiber microwebs are indistinguishable from the microfibers 12 of the carrier web. FIG. 6 is an enlarged view of a nonwoven web containing a microfiber microweb 13, conventional staple polyester fibers 14, and thermally bondable fibers 15.

Melt blown microfiber webs containing the microfiber microwebs of the invention can be prepared using, for example, the apparatus described in U.S. Pat. No. 4,118,531 (Hauser) or U.S. Pat. No. 4,429,001 (Kolpin et al.), which references are incorporated herein for that purpose.

When using the apparatus described in Hauser, the microfiber source web is merely substituted for the web of crimped bulking fibers and the microfiber source web is divellicated by the lickerin of the apparatus to form the microfiber microwebs. The microfiber microwebs are then conveyed by an air stream into the stream of blown carrier microfibers where they become mixed with the blown carrier microfibers. The stream of blown carrier microfibers and microfiber microwebs then continues to the collector where the web of blown carrier microfibers and microfiber microwebs is formed.

When using the apparatus described in Kolpin et al., the microfiber source web is divellicated and the resulting microfiber microwebs are collected as described hereinabove.

The microfiber microwebs can then be substituted for the sorbent particles of Kolpin et al. A stream of microfiber microwebs is fed into a single stream of blown carrier microfibers or into two streams of blown carrier microfibers where the microfiber microwebs become mixed with the blown carrier microfibers. The stream of blown carrier microfibers and microfiber microwebs then continues to the collector where the web of blown carrier microfibers and microfiber microwebs is formed.

Staple fibers, such as liquid-sorbent transport fibers as disclosed in European Patent Publication No. 0 156 649 which is incorporated by reference herein for that purpose, or crimped bulking fibers, as disclosed in U.S. Pat. No. 4,118,531, which is incorporated herein by reference for that purpose, can also be dispersed in the web of blown microfibers by adding the staple fibers to the stream of blown microfibers and microfiber microwebs prior to collection or by combining the staple fibers with the microfiber microwebs at the lickerin as the microfiber microwebs are being formed.

The effective average diameter of the carrier microfibers of the blown microfiber web is generally less than about 10 microns and more preferably about 5 to 10 microns. The effective fiber diameter is calculated according to the method set forth in Davies, C. N., "The Separation of Airborne Dust and Particles," Institution of Mechanical Engineers, London, Proceedings 1B, 1952. The diameter of the microfibers in the microfiber microweb can be similar in diameter to, or smaller than, the microfibers of the blown carrier web. Preferably, when the microfiber microweb contains sorbent particles, the average effective diameter of the microfibers of the microweb is less than about 10 microns. Very small fibers, having an effective diameter averaging less than 5 or even 1 micron are useful, particularly with small sorbent particles, e.g., those particles having an average effective diameter of less than 0.1 microns. The microfibers of the microfiber microwebs can be smaller in diameter than is normally considered suitable for use in microfiber webs, since the staple fibers or the blown carrier microfibers in the nonwoven webs contribute to the strength of the nonwoven webs. When the microfiber carrier web having the microfiber microwebs dispersed therein is to be used as a sorbent material, the microfiber microweb fibers are preferably smaller in diameter than the fibers of the blown carrier microfibers, e.g., at least 20% smaller and more preferably at least 50% or more smaller. The smaller microfiber microweb fibers increase the capillary action in the microfiber microwebs, enhancing sorptive properties.

The weight of the nonwoven web of blown carrier microfibers and microfiber microwebs can vary widely depending on the end use of the web. Generally, when the nonwoven web is to be used as sorbent material, the weight of the web can range from 50 to 1000 g/m$^2$. When the nonwoven web is to be used as thermal insulation, the weight of the web is generally in the range of 50 to 500 g/m$^2$. The weight of the nonwoven web is generally in the range of about 50 to 600 g/m$^2$ when the web is to be used for filtration purposes.

The amount of microfiber microwebs in the nonwoven web of blown carrier microfibers and microfiber microwebs can also vary widely. Generally, the microfiber microwebs comprise about 10 to 90 weight percent, more preferably 30 to 90 weight percent, of the nonwoven web when the web is for use as a sorbent material. Generally, the microfiber microwebs comprise about 20 to 80 weight percent, more preferably 40 to 80 weight percent, of the nonwoven web when the web is for use as thermal insulation. For filtration purposes, the nonwoven web generally contains about 10 to 90 weight percent, more preferably 30 to 80 weight percent microfiber microwebs.

When staple fibers are incorporated into the nonwoven web of blown carrier microfibers and microfiber microweb, they may comprise from about 5 to 80 weight percent of the nonwoven web.

Air-laid staple fiber webs containing the microfiber microwebs of the invention can be prepared using conventional air-laying apparatus, which are well-known in the art. Typical of such apparatus is the Rando Webber ™ air-laying apparatus, available from the Rando Machine Company. Air-laying apparatus is described, for example, in U.S. Pat. No. 2,800,497 (Langdon et al.). In such apparatus, staple fiber is fed into a hopper, picked apart, and delivered to a first rotary condenser or conveyor screen.

In conventional staple fiber air-laying, the fiber batt formed at the condenser or conveyor screen is picked apart into individualized fibers by a lickerin, the individualized fibers then being delivered by means of an air stream to a second rotary condenser which forms the final web which is then collected.

In the present invention, the microfiber source web is fed to the staple fiber batt at the feed roll after the staple fiber batt is formed at the first rotary condenser. This layered composite is then fed to the lickerin where the microfiber microwebs are formed from the microfiber source web and the staple fibers are individualized. These microfiber microwebs and staple fibers are then mixed in the air stream and delivered to the second rotary condenser, formed into the nonwoven web and collected.

The weight of the nonwoven web of staple carrier fibers and microfiber microwebs can vary widely depending on the end use of the web. Generally, when the nonwoven web is to be used as sorbent material, the weight of the web can range from 50 to 1000 g/m$^2$. When the nonwoven web is to be used as thermal insulation, the weight of the web is generally in the range of 50 to 500 g/m$^2$. The weight of the nonwoven web is generally in the range of about 50 to 600 g/m$^2$ when the web is to be used for filtration purposes.

The amount of microfiber microwebs in the nonwoven web of staple carrier fibers and microfiber microwebs can also vary widely. Generally, the microfiber microwebs comprise about 10 to 90 weight percent, more preferably 20 to 80 weight percent, of the nonwoven web when the web is for use as a sorbent material. Generally, the microfiber microwebs comprise about 20 to 80 weight percent, more preferably 40 to 80 weight percent, of the nonwoven web when the web is for use as thermal insulation. For filtration purposes, the nonwoven web generally contains about 10 to 90 weight percent, more preferably 20 to 80 weight percent microfiber microwebs.

Staple fibers suitable for use in the air-laid web include natural fibers, such as cotton and wool, and synthetic fibers, such as polyesters, polyamides, acrylics, polyolefins, rayon, acetate, and blends thereof.

The integrity of the air-laid webs can be increased by needle-tacking the web, by applying a binder material to the web, or by incorporating thermally bondable binder fibers in the web, each method being well-known to those skilled in the art. The integrity of the air-laid webs can also be increased by partial fusion of the microfiber microwebs. This method is particularly useful when the thermoplastic polymer from which the microfiber microwebs are formed has a lower melting point than the carrier fibers of the air-laid web, for example, when the microfiber microwebs are formed from polypropylene and the carrier fibers are polyethylene terephthalate fibers.

Air-laid webs containing wood pulp fiber as the carrier fiber and microfiber microwebs can be prepared using conventional apparatus. Wood pulp which is generally supplied in condensed sheet form is separated into individualized wood pulp fibers by conventional means, e.g., a hammer mill, and delivered to a first air stream. A source web is divellicated to form microfiber microwebs and delivered to a second air stream. The air streams are combined, causing the wood pulp fibers and microfiber microwebs to mix. The mixed wood pulp carrier fibers and the microfiber microwebs are collected in the manner conventionally used to collect wood pulp batts.

Air-laid webs containing wood pulp fiber as the carrier fiber and microfiber microwebs are useful preferably as sorbent materials. Generally, the amount of microfiber microweb in such webs is in the range of 10 to 90 weight percent, preferably 20 to 75 weight percent.

The nonwoven webs formed by the melt blowing process or by the air-laying process may vary widely in thickness, e.g., from about 0.02 to 4 cm. For some applications, two or more separately formed webs of the invention may be assembled as one thicker web. Also melt blown nonwoven webs of the invention may be prepared by depositing the stream of melt blown fibers and microfiber microwebs onto another similar or dissimilar web which is to form part of the eventual web product. Other structures, such as impermeable films, can be laminated to a nonwoven web of the invention through mechanical engagement, heat bonding, or adhesives.

Nonwoven webs of the invention may be further processed after collection, e.g., compacting through heat and pressure to control sheet caliper, to give the sheet product a pattern, or to increase the integrity of the web.

The microfiber microwebs of the invention are also useful in liquid sorbent shaped articles wherein the microfiber microwebs are loosely contained within a covering or are dispersed in a nonwoven web which is incorporated in a covering, e.g., in particulate form. The covering may be of any porous material which permits contact of the microwebs with the liquid to be sorbed. Such covering material includes, for example woven, knitted, and nonwoven fabrics, paper, screening, etc. Nonwoven stretch fabrics are particularly preferred porous covering materials. The shape of the covering prepared from the porous material determines the shape of the liquid-sorbent shaped article. The covering may be of any desired size or shape, in such shapes as pillows, pouches, tubes, blocks, balls, and pyramids. The microfiber microwebs for use in these shaped articles may also contain sorbent particulate material.

The liquid-sorbent shaped articles can be prepared by forming the covering of the porous material in the desired shape, depositing microfiber microwebs into the porous material covering and closing the container, if desired.

The following examples further illustrate this invention, but the particular materials and amounts thereof in these examples, as well as the conditions and details, should not be construed to unduly limit this invention. In the examples, all parts and percentages are by weight unless otherwise specified.

In the examples, the following test methods were used:

Thickness

The thickness of samples is determined using a low-load caliper tester Model No. CS-49-051, available from Custom Scientific Instruments, Inc., with a 1.22 g balance weight.

Demand Sorbency Test

A 4.45 cm (1.75 inch) in diameter test sample of sorbent web is placed on a 25–50 micron porous plate in a filter funnel. A pressure of 1.0 kPa is applied to the sample by a plunger which is freely movable in the barrel of the funnel. Test fluid at zero hydrostatic head is conducted from a reservoir through a siphon mechanism to the upper surface of the porous plate where the test sample sorbs the test fluid. The initial lineal rate of absorbency is determined and reported in ml/min.

Centifugal Retention Test

A sample of web, saturated to equilibrium saturation, in the demand sorbency test funnel is placed in a centrifuge tube which is placed in a centrifuge and subjected to a centrifugal force of 180 G for 10 minutes. The samples are removed and the amount of test solution retained is determined.

Drip Capacity Test

A sample of web, 10 cm × 10 cm, is placed on a liquid impervious plate set at a 45° angle. Test liquid is pumped onto the sample from a height of 2 cm to a point 2 cm from the top and 5 cm from each side edge of the sample. The sample fails when fluid discharges from the lower edge of the sample. The drip capacity is the amount of fluid retained per unit sample weight to the point of failure.

Oil Sorbency

A sample of web, 21.6 cm × 27.9 cm, is placed in a tray, containing a drain screen in the bottom thereof and mineral oil having a viscosity of 50–60 SUS at 38° C. to a depth of at least 25 mm, on the surface of the oil. The sample is allowed to rest on the surface of the oil for one minute and, if not saturated, is submerged in the oil. After an additional two minutes, the sample is removed from the oil using the drain screen and is allowed to drain for two minutes. The amount of oil remaining in the sample is determined. The oil sorption is the amount of oil remaining in the sample per sample weight (g/g).

Thermal Resistance

A sample of web is tested on a guarded hot plate as described in ASTM Test Method D1518-64 with the test sample subjected to a force of 14.5 Pa during testing.

Filtration Performance

Filtration performance of a web is evaluated by testing for aerosol penetration of dioctyl phthalate (DOP) particles. DOP penetration data is obtained using a Model Q127 DOP Pentrometer, available from Air Techniques, Inc., set at a flow rate of 32 l/min on a filter face area of 100 cm$^2$ and generating an aerosol of 0.3 micron DOP particles at a mass concentration of 100 mg/m$^3$. The DOP penetration is measured by comparison of upstream and downstream aerosol concentrations using light scattering photometry.

In the tests where synthetic urine was used as the test fluid, synthetic urine having a conductance of 15.7 $\mu\Omega^{31}$ $^1$·cm$^{-1}$ was prepared according to the following formula:

| | |
|---|---|
| 0.6% | calcium chloride |
| 0.10% | magnesium sulfate |
| 0.83% | sodium chloride |
| 1.94% | urea |
| 97.07% | deionized water |

EXAMPLES 1-4

A blown microfiber source web was prepared from polypropylene pellets, type 35 MF available from Exxon Corp., using conventional melt blowing apparatus. The microfibers had an effective fiber size of 5 microns. The web had a basis weight of 400 g/m$^2$, a thickness of 0.4 cm, and a density of 0.1 g/cm$^3$. This microfiber source web was divellicated to form microfiber microwebs using a coarse lickerin (2.9 teeth/cm$^2$) or a fine lickerin (6.2 teeth/cm$^2$) at lickerin speeds of 900 rpm or 2400 rpm as set forth in Table 1. The size of the nuclei and the total maximum microweb diameter were measured for each of 10 microfiber microwebs from each source web. The results, averages and ranges, are set forth in Table 1.

TABLE 1

| | Lickerin | | Microweb | | | |
|---|---|---|---|---|---|---|
| | | Speed | Nuclei diameter (mm) | | Microweb diameter (mm) | |
| Ex. | Teeth | (rpm) | avg | range | avg | range |
| 1 | coarse | 900 | 1.05 | 0.95–1.16 | 1.52 | 1.38–1.63 |
| 2 | coarse | 2400 | 1.21 | 1.11–1.27 | 1.76 | 1.59–1.90 |
| 3 | fine | 900 | 0.56 | 0.40–0.63 | 1.24 | 1.03–1.59 |
| 4 | fine | 2400 | 0.63 | 0.48–0.79 | 1.06 | 0.95–1.27 |

As can be seen from the diameters of the microwebs and the microweb nuclei, coarse lickerin teeth produce larger microwebs than fine lickerin teeth, faster lickerin speed produces larger microwebs, and the relative size of the nuclei to the total microweb size is greater when coarse teeth and/or faster speed are used.

EXAMPLES 5-8

A microfiber web was prepared from polypropylene pellets as in Examples 1-4 except that the web had a basis weight of 50 g/m$^2$, a thickness of 0.2 mm, and a bulk density of 0.25 g/cm$^3$. A composite microfiber source web was prepared by combining eight layers of this web resulting in a composite source web having a basis weight of 400 g/m$^2$. This source web was divellicated and evaluated as in Examples 1-4. The results are set forth in Table 2.

TABLE 2

| | Lickerin | | Microweb | | | |
|---|---|---|---|---|---|---|
| | | Speed | Nuclei diameter (mm) | | Microweb diameter (mm) | |
| Ex. | Teeth | (rpm) | avg | range | avg | range |
| 5 | coarse | 900 | 1.17 | 1.05–1.27 | 1.30 | 1.21–1.40 |
| 6 | coarse | 2400 | 1.27 | 1.11–1.43 | 1.37 | 1.21–1.52 |
| 7 | fine | 900 | 0.75 | 0.63–0.86 | 0.86 | 0.71–1.03 |
| 8 | fine | 2400 | 0.73 | 0.67–0.79 | 0.79 | 0.71–0.89 |

As was seen from the data in Table 1, the data Table 2 shows that coarse lickerin teeth produce larger microwebs than fine lickerin teeth. In this series, the speed of the lickerin had little effect on the size of the microwebs and relative size of the nuclei to the total microweb size were similar within the series, but larger than obtained in Examples 1-4.

EXAMPLES 9-14

Microfiber source webs I and II were prepared from polypropylene pellets, type 35 MF, available from Exxon Corp., and synthetic sorbent particulate J-550, available from Grain Processing Corp., using the apparatus of Kolpin et al., supra. Microfiber source web I had a basis weight of 100 g/m$^2$, a thickness of 0.3 cm, and contained 50 weight percent polypropylene microfiber having an effective fiber size of 5 microns and 50 weight percent synthetic sorbent particulate. Microfiber source web II had a basis weight of 150 g/m$^2$, a thickness of 0.4 cm, and contained 33.3 weight percent polypropylene microfiber having an effective fiber size of 5 microns and 66.7 weight percent synthetic sorbent particulate. Each source web was sprayed with 2 percent, based on the weight of the web microfiber, Triton ™ X-100 surfactant, available from Rohm and Haas Co. Nonwoven blown microfiber webs were prepared using the apparatus described in Hauser, supra, with a lickerin having fine teeth and a tooth density of 6.2 teeth/cm$^2$ at a rate of 2400 rpm to divellicate the source web and produce sorbent microfiber microwebs. The carrier web microfibers were prepared from polypropylene pellets, type 35 MF available from Exxon Corp. and had an effective fiber diameter of 8 microns. The composition of each blown microfiber web is set forth in Table 3. Each web was tested for demand absorbency and retention using synthetic urine as the test fluid. The results are set forth in Table 3.

TABLE 3

| Example | Basis weight (g/m$^2$) | Microweb | Microweb content (%) | Carrier web content (%) | Demand sorbency (ml/min) | Retention (g/g) |
|---|---|---|---|---|---|---|
| 9 | 134 | I | 25 | 75 | 2.9 | 3.5 |
| 10 | 133 | II | 25 | 75 | 3.6 | 4.2 |
| 11 | 200 | I | 50 | 50 | 5.1 | 5.5 |
| 12 | 200 | II | 50 | 50 | 5.7 | 7.2 |
| 13 | 400 | I | 75 | 25 | 8.2 | 7.8 |
| 14 | 400 | II | 75 | 25 | 9.5 | 10.0 |

As can be seen from the data in Table 3, at comparable basis weights and microweb contents, webs containing microweb II which was denser and contained a greater proportion of sorbent particulate than microweb I, had higher demand sorbency and retention. Increasing basis weight and microweb content also showed higher demand sorbency and retention.

EXAMPLES 15-16 and Comparative Examples C1-C2

A microfiber source web was prepared from polypropylene pellets, type 35 MF available from Exxon Corp., using conventional melt blowing apparatus. The microfiber source web had a basis weight of 400 g/m², a thickness of 0.4 cm, and the microfibers of the source web had an effective fiber size of 5 microns. The source web was sprayed with 2 percent, based on the weight of the web, Triton TM X-100 surfactant, available from Rohm and Haas Co. In Examples 15-16, nonwoven blown microfiber webs were prepared using the apparatus described in Hauser, supra, with a lickerin having fine teeth and a tooth density of 6.2 teeth/cm² at a rate of 2400 rpm to divellicate the source web and produce sorbent microfiber microwebs. A web of sorbent fibers, Lanseal TM, 7 denier, 5.1 cm long, available from Japan Exlan Co., Ltd., was also introduced at the lickerin. The carrier web microfibers were prepared from polypropylene pellets, type 35 MF available from Exxon Corp., and had an effective fiber diameter of 8 microns. In Comparative Examples C1 and C2, nonwoven microfiber webs were prepared in the same manner as in Examples 15-16, except that no source web was introduced at the lickerin. The composition of each blown microfiber web is set forth in Table 4. Each web was tested for demand absorbency, retention, and drip capacity (pump rate of 10 ml/min) using synthetic urine as the test fluid. The results are set forth in Table 4.

TABLE 4

| Ex. | Sorbent fiber content (g/m²) | Microweb content (g/m²) | Carrier web content (g/m²) | Demand sorbency (ml/min) | Retention (g/g) | Drip capacity (g/g) |
|---|---|---|---|---|---|---|
| 15 | 60 | 60 | 100 | 7.0 | 2.8 | nt* |
| C1 | 60 | 0 | 100 | 5.4 | 2.7 | nt* |
| 16 | 100 | 100 | 100 | 8.4 | 4.1 | 7.5 |
| C2 | 100 | 0 | 100 | 6.6 | 4.0 | 4.7 |

*not tested

As can be seen from the data in Table 4, the addition of microwebs to nonwoven webs of blown microfibers and staple sorbent fibers increased the demand sorbency but had little effect on retention. However, in the samples tested, the addition of microwebs significantly improved the drip capacity.

EXAMPLES 17-19 and Comparative Example C3

A microfiber source web was prepared from polypropylene pellets, type 35 MF available from Exxon Corp., using conventional melt blowing apparatus. The microfiber source web had a basis weight of 150 g/m², a thickness of 0.2 cm, and the microfibers of the source web had an effective fiber size of 5 microns. The source web was sprayed with 2 percent, based on the weight of the web microfibers, Triton TM X-100 surfactant, available from Rohm and Haas Co. In Examples 17-19, the source web was introduced in a Rando Webber TM air-laying apparatus at the feed roll to the lickerin, with a 50:50 blend of polyethylene terephthalate fibers, 15 denier, 3.8 cm long, and thermally bondable Chisso TM fibers, 4 denier, 3.2 cm long, available from Chisso Corp. This composite web was then fed to the lickerin which had fine teeth, a tooth density of 6.2 teeth/cm², and rotated at a rate of 1200 rpm. The lickerin divellicated the source web and individualized the staple fibers which were then air-laid to form a nonwoven web. The nonwoven web was then heated in an oven for one minute at 138° C., to effect thermobonding of the thermally bondable Chisso TM fiber at points of contact. The web of Comparative Example 3 was prepared in the same manner as Examples 17-19, except that no source web was introduced at the condenser. The composition of each thermally bonded web is set forth in Table 5. Each web was tested for demand absorbency, retention, and drip capacity (pump rate of 10 ml/min) using synthetic urine as the test fluid. The results are set forth in Table 5.

TABLE 5

| Ex. | Microweb content (g/m²) | Carrier web content (g/m²) | Demand absorbency (ml/min) | Retention (g/g) | Drip capacity (g/g) |
|---|---|---|---|---|---|
| C3 | 0 | 130 | 0.6 | 0.2 | 0.5 |
| 17 | 72 | 130 | 3.6 | 0.4 | 0.5 |
| 18 | 108 | 130 | 6.0 | 0.5 | 0.8 |
| 19 | 240 | 130 | 8.0 | 0.7 | 1.4 |

As can be seen from the data in Table 5, increasing amounts of microwebs in a staple fiber air-laid web progressively improves demand sorbency, retention, and drip capacity.

EXAMPLES 20-22 AND COMPARATIVE EXAMPLE C4

In Examples 20-22, nonwoven air-laid webs were prepared as in Examples 17-19, except the compositions were as set forth in Table 6. In Comparative Example C4, the microweb material was omitted. The basis weight and thickness were as set forth in Table 6.

TABLE 6

| Example | Basis weight (g/m²) | Thickness (cm) | Carrier web content (%) | Microweb content (%) |
|---|---|---|---|---|
| C4 | 133 | 2.1 | 100 | 0 |
| 20 | 219 | 2.4 | 61 | 39 |
| 21 | 235 | 1.9 | 57 | 43 |
| 22 | 357 | 2.7 | 37 | 63 |

Each web was tested for thermal resistance and from this value the thermal resistance per cm thickness was calculated. The results are set forth in Table 7.

TABLE 7

| Example | Thermal resistance (Clo) | Clo/cm |
|---|---|---|
| C4 | 2.0 | 0.9 |
| 20 | 2.8 | 1.2 |
| 21 | 2.7 | 1.4 |
| 22 | 3.7 | 1.4 |

As can be seen from the data in Table 7, increased amounts of microweb improved thermal resistance. The webs of the invention, Examples 20-22, had superior thermal resistance per cm thickness when compared to Comparative Example C4, even though the webs of the invention were more dense.

EXAMPLES 23-27

In Examples 23-27, nonwoven melt blown microfiber webs containing microwebs were prepared using microwebs and apparatus as in Examples 15-16, with the compositions set forth in Table 8. The basis weight and thickness of each sample was determined, the results being set forth in Table 8.

TABLE 8

| Example | Basis weight (g/m²) | Thickness (cm) | Carrier web content (%) | Microweb content (%) |
|---|---|---|---|---|
| 23 | 307 | 0.96 | 36 | 64 |
| 24 | 259 | 0.81 | 20 | 80 |
| 25 | 215 | 0.70 | 25 | 75 |
| 26 | 207 | 0.64 | 50 | 50 |
| 27 | 164 | 0.57 | 33 | 67 |

Each web was tested for thermal resistance and from this value the thermal resistance per cm thickness was calculated. The results are set forth in Table 9.

TABLE 9

| Example | Thermal resistance (Clo) | Clo/cm |
|---|---|---|
| 23 | 1.7 | 1.8 |
| 24 | 1.4 | 1.7 |
| 25 | 1.2 | 1.7 |
| 26 | 1.1 | 1.8 |
| 27 | 1.0 | 1.8 |

As can be seen from the data in Table 9, excellent thermal resistance can be achieved with the webs of the invention using various basis weights, thicknesses, and microweb contents.

EXAMPLES 28–30 AND COMPARATIVE EXAMPLES C5–C7

A microfiber source web was prepared from polypropylene pellets, type 35 MF available from Exxon Corp., using conventional melt blowing apparatus. The microfiber source web had a basis weight of 400 g/m², a thickness of 0.4 cm, and the microfibers of the source web had an effective fiber size of 5 microns. The source web was sprayed with 2 percent, based on the weight of the web, Triton TM X-100 surfactant, available from Rohm and Haas Co. In Examples 28–30, nonwoven blown microfiber webs were prepared using the apparatus described in Hauser, supra, with a lickerin having fine teeth and a tooth density of 6.2 teeth/cm² at a rate of 1200 rpm to divellicate the source web and produce sorbent microfiber microwebs. The carrier web microfibers were prepared from polypropylene pellets, type 35 MF available from Exxon Corp., and had an effective fiber diameter of 8 microns. In Comparative Examples C5–C7, nonwoven microfiber webs were prepared in the same manner as in Examples 28–30, except that no source web was introduced at the lickerin. The composition of each blown microfiber web is set forth in Table 10. Each web was tested for drip capacity (pump rate of 40 g/min) using synthetic urine as the test fluid. The results are set forth in Table 10.

TABLE 10

| Ex. | Basis weight (g/m²) | Thickness (mm) | Density (g/cm³) | Carrier web content (%) | Microweb content (%) | Drip capacity (g/g) |
|---|---|---|---|---|---|---|
| C5 | 200 | 2 | 0.10 | 100 | 0 | 0.09 |
| 28 | 200 | 3 | 0.07 | 50 | 50 | 0.14 |
| C6 | 400 | 4 | 0.10 | 100 | 0 | 0.21 |
| 29 | 400 | 6 | 0.07 | 25 | 75 | 0.25 |
| C7 | 1000 | 10 | 0.10 | 100 | 0 | 0.20 |

TABLE 10-continued

| Ex. | Basis weight (g/m²) | Thickness (mm) | Density (g/cm³) | Carrier web content (%) | Microweb content (%) | Drip capacity (g/g) |
|---|---|---|---|---|---|---|
| 30 | 1000 | 14 | 0.07 | 10 | 90 | 0.30 |

As can be seen from the data in Table 10, substituting microfiber microwebs for a portion of the microfiber in a blown microfiber web provides a significant increase in the drip capacity of the webs. The webs of Examples 28, 29, and 30 show increased drip capacities of 56%, 19%, and 50%, respectively, over the webs of Comparative Examples C5, C6, and C7 despite the fact that a microfiber material, i.e., the microfiber microwebs, is being substituted for microfiber material.

EXAMPLES 31–34 AND COMPARATIVE EXAMPLE C8

A microfiber source web was prepared from polypropylene pellets, type 35 MF available from Exxon Corp., using conventional melt blowing apparatus. The microfiber source web had a basis weight of 400 g/m², a thickness of 0.4 cm, and the microfibers of the source web had an effective fiber size of 5 microns. The source web was sprayed with 2 percent, based on the weight of the web, Triton TM X-100 surfactant, available from Rohm and Haas Co. In Examples 31–34, nonwoven blown microfiber webs were prepared using the apparatus described in Hauser, supra, with a lickerin having fine teeth and a tooth density of 6.2 teeth/cm² at a rate of 1200 rpm to divellicate the source web and produce sorbent microfiber microwebs. A web of polyethylene terephthalate staple fibers, 15 denier, 3.8 cm long, was also introduced at the lickerin. The carrier web microfibers were prepared from polypropylene pellets, type MF available from Exxon Corp., and had an effective fiber diameter of 8 microns. The resulting carrier web was a 50/50 blend of carrier web microfibers and polyethylene terephthalate staple fibers. In Comparative Example C8, a nonwoven microfiber web was prepared in the same manner as in Examples 31–34 except that no source web was introduced at the lickerin. The composition of each blown microfiber web is set forth in Table 11. Each web was tested for drip capacity (pump rate of 40 g/min) using synthetic urine as the test fluid. The results are set forth in Table 11.

TABLE 11

| Example | Carrier web content (g/m²) | Microweb content (g/m²) | Thickness (mm) | Density (g/cm³) | Drip capacity (g/g) |
|---|---|---|---|---|---|
| C8 | 200 | 0 | 12 | 0.02 | 0.03 |
| 31 | 200 | 50 | 13 | 0.02 | 0.04 |
| 32 | 200 | 100 | 13 | 0.02 | 0.05 |
| 33 | 200 | 200 | 14 | 0.03 | 0.07 |
| 34 | 200 | 300 | 14 | 0.04 | 0.09 |

As can be seen from the data in Table 11, webs show increasing drip capacity, on a g/g basis, as the amount of microwebs in the web increases. Examples 31–34 show increased drip capacity over that of Comparative Example C8 of 33%, 67%, 133%, and 200%, respectively.

EXAMPLE 35 AND COMPARATIVE EXAMPLE C9

A microfiber source web was prepared from polypropylene pellets, type 35 MF available from Exxon Corp., using conventional melt blowing apparatus. The microfiber source web had a basis weight of 400 g/m², a thickness of 0.4 cm, and the microfibers of the source web had an effective fiber size of 5 microns. The source web was sprayed with 2 percent, based on the weight of the web, Triton™ X-100 surfactant, available from Rohm and Haas Co. In Example 35, nonwoven blown microfiber webs were prepared using the apparatus described in Hauser, supra, with a lickerin having fine teeth and a tooth density of 6.2 teeth/cm² at a rate of 1200 rpm to divellicate the source web and produce sorbent microfiber microwebs. The carrier web microfibers were prepared from polypropylene pellets, type 35 MF available from Exxon Corp., and had an effective fiber diameter of 8 microns. In Comparative Example C9, nonwoven microfiber webs were prepared in the same manner as in Example 35, except that no source web was introduced at the lickerin. The composition of each blown microfiber web is set forth in Table 12. Each web was tested for oil sorbency and drip capacity (pump rate of 16 g/min) using mineral oil as the test fluid. The results are set forth in Table 12.

TABLE 12

| Ex. | Basis weight (g/m²) | Thickness (mm) | Density (g/cm³) | Carrier web content (%) | Microweb content (%) | Oil sorbency (g/g) | Drip capacity (g/g) |
| --- | --- | --- | --- | --- | --- | --- | --- |
| C9 | 210 | 2 | 0.11 | 100 | 0 | 9.4 | 5.1 |
| 35 | 240 | 3 | 0.08 | 20 | 80 | 24.0 | 23.3 |

As can be seen from the data in Table 12, the web of Example 35 shows a significant increase in both oil sorbency and drip capacity, on a g/g basis, over the web of Comparative Example C9. The increase in oil sorbency was 155%, while the increase in drip capacity was 357%.

EXAMPLES 36 AND 37

A microfiber source web was prepared from polypropylene pellets, type 35 MF, available from Exxon Corp., and activated charcoal, type BPL 30×140, available from Calgon Co., using the apparatus of Kolpin et al., supra. The microfiber source web had a basis weight of 190 g/m², a thickness of 1.5 cm, and contained 76 weight percent polypropylene microfiber having an effective fiber size of 7 microns and 24 weight percent activated charcoal. Nonwoven blown microfiber webs were prepared using the apparatus described in Hauser, supra, with a lickerin having a tooth density of 6.2 fine teeth/cm² at a rate of 1200 rpm to divellicate the source web and produce microfiber microwebs. The carrier web microfibers were prepared from polypropylene pellets, type 34 MF, available from Exxon Corp., and had an effective fiber diameter of 9 microns. The nonwoven webs had the physical characteristics set forth in Table 13.

TABLE 13

| Example | Basis weight (g/m²) | Thickness (mm) | Density (g/cm³) | Carrier web content (%) | Microweb content (%) |
| --- | --- | --- | --- | --- | --- |
| 36 | 183 | 2.0 | 0.09 | 49 | 51 |
| 37 | 270 | 2.5 | 0.11 | 33 | 67 |

Each of these webs containing activated charcoal was suitable for use as a filtration device.

EXAMPLE 38

A nonwoven blown microfiber web was prepared using the microwebs and apparatus as in Examples 15-16, except the web had a basis weight of 200 g/m², a thickness of 3 mm, and the web contained 25 weight percent carrier microfiber having an effective fiber diameter of 8 microns and 75 weight percent microfiber microwebs, the microfibers of which had an effective diameter of 5 microns. The web was tested for filtration performance and was found to have a DOP value of 38% at a pressure drop of 2 mm water.

EXAMPLES 39-40 AND COMPARATIVE EXAMPLE C10

A source web was prepared from polypropylene pellets, type 35 MF available from Exxon Corp., and synthetic sorbent particulate J-550, available from Grain Processing Corp., using the apparatus of Kolpin et al., supra. The microfiber source web contained 55 weight percent blown microfibers and 45 weight percent sorbent particulate and had a basis weight of 200 g/m², a thickness of 3 mm, and the microfibers of the source web had an effective fiber size of 5 microns. The source web was sprayed with 2 percent, based on the weight of the web microfiber, Triton™ X-100 surfactant, available from Rohm and Haas Co. In Examples 39-40, the source web and fibrillated wood pulp fibers obtained by fibrillating bleached kraft wood pulp, available from ITT Rayonier, Inc., were introduced into a Rando Webber™ air-laying apparatus at the feed roll to the lickerin in amounts such that the web of Example 39 contained 75 weight percent wood pulp fiber and 25 weight percent microwebs and the web of Example 40 contained 50 weight percent wood pulp fiber and 50 weight percent microwebs. The lickerin, which had a tooth density of 6.2 teeth/cm² and rotated at a rate of 1200 rpm, divellicated the source web to form microfiber microwebs and the microwebs and the fibrillated wood pulp fibers were mixed and collected as a web. In Comparative Example C10, a web was prepared as in Examples 39-40 except no source web was added. The webs were tested for demand sorbency, retention, and drip capacity (pump rate of 39 g/min). The results are set forth in Table 14.

TABLE 14

| Ex. | Basis weight (g/m²) | Density (g/cm³) | Demand sorbency (ml/min) | Retention (g/g) | Drip capacity (g/g) |
| --- | --- | --- | --- | --- | --- |
| C10 | 445 | .035 | 6.4 | 0.97 | 0.3 |
| 39 | 410 | .050 | 8.0 | 2.27 | 6.5 |

TABLE 14-continued

| Ex. | Basis weight (g/m²) | Density (g/cm³) | Demand sorbency (ml/min) | Retention (g/g) | Drip capacity (g/g) |
|---|---|---|---|---|---|
| 40 | 425 | .039 | 7.1 | 3.28 | 25.5 |

As can be seen from the data in Table 14, addition of microwebs containing sorbent particulate to the wood pulp web increases demand sorbency, retention, and drip capacity of the web.

EXAMPLES 41 AND 42

A source web was prepared from polypropylene pellets, type 35 MF available from Exxon Corp., using conventional apparatus. The microfiber source web had a basis weight of 275 g/m², a thickness of 3 mm, a density of 0.09 g/cm³, and the microfibers of the source web had an effective fiber size of 7 microns. The source web was sprayed with 2 percent, based on the weight of microfiber, Aerosol ™ OT surfactant, available from American Cyanamid Co. The source web was divellicated by a lickerin, which had a tooth density of 6.2 teeth/cm² and rotated at a rate of 1200 rpm, to form microfiber microwebs. The divellicated microwebs were fed by an air stream into nonwoven material prepared to contain the microwebs. For the nonwoven containers, a nonwoven stretch fabric was prepared according to the teachings of U.S. Pat. No. 4,551,378 using Chisso ™ ES fibers, 1.5 denier, 3.8 cm long, available from Chisso Corp. The material had a basis weight of 80 g/m², a thickness of 4 mm, and a bulk density of 0.02 g/cm³. For the container of Example 41, a rectangular pouch was prepared from two pieces of the material, each 23 cm×38 cm, sealed along three edges by heat bonding. For the container of Example 42, the two long edges of a rectangular piece of the material, 24 cm×122 cm, were brought together and sealed by heat bonding to form a cylinder having a diameter of about 8 cm. One end of the cylinder was also sealed. The pouch of Example 41 was filled with about 150 g microwebs through the open end then that end was also sealed. When placed in a bath of tap water at about 22° C., the microweb-filled pouch sorbed about 2270 g of the tap water. The cylinder of Example 42 was filled with about 340 g microwebs through the open end and then that end was also sealed. When placed in a bath of tap water at about 22° C., the microweb-filled cylinder sorbed about 3060 g of the tap water.

EXAMPLES 43–49

A source web was prepared from polypropylene pellets, type 35 MF, available from Exxon Corp., using conventional apparatus. The microfiber source web had a basis weight of 270 g/m², a thickness of 3 mm, a density of 0.09 g/cm³, and the microfibers of the source web had an effective fiber size of 7 microns. The source web was sprayed with 2 percent, based on the weight of microfiber, Aerosol ™ OT surfactant, available from American Cyanamid Co. The source web was divellicated by a lickerin, having a tooth density of 6.2 teeth/cm² and rotating at a rate of 1200 rpm, to form microfiber microwebs. Nonwoven stretch fabric was prepared according to the teachings of U.S. Pat. No. 4,551,378 using Chisso ™ ES fibers, 1.5 denier, 3.8 cm long, available from Chisso Corp. The fabric had a basis weight of 80 g/m² and a thickness of 4 mm. Cylinders were prepared from the stretch fabric, each cylinder being approximately 25 cm long, 8 cm in diameter, and weighing about 5 g. One end of each cylinder was heat sealed. The prepared microfiber microwebs were fed by an air stream into the open end of each cylinder and the open end then sealed. The gross weight of the cylinder and the microfiber microwebs is set forth in Table 15.

The microfiber microweb-containing cylinders were then tested for sorbency of various liquids according to ASTM Test Method F726-81 except that the point of saturation was determined visually rather than by elapsed time and the drain time was 1 minute. A cylinder was placed on a metal screen (0.08 cm thick, 0.48 cm hole size, and 50% open) and this test assembly was lowered into the test liquid. The assembly was removed from the test liquid after saturation and allowed to drain for one minute. The amount of sorbed test liquid was then determined. The test liquid, the amount of test liquid sorbed, and the weight ratio of liquid sorbed to cylinder weight is set forth in Table 15.

TABLE 15

| Example | Test liquid | Cylinder-microweb weight (g) | Liquid sorbed (g) | Wt ratio liquid/cylinder |
|---|---|---|---|---|
| 43 | water | 58 | 609 | 10.5 |
| 44 | ethylene glycol | 53 | 693 | 13.1 |
| 45 | 1:1 water/ethylene glycol | 52 | 625 | 12.0 |
| 46 | 1 N sulfuric acid | 54 | 628 | 11.6 |
| 47 | 0.1 N sodium hydroxide | 65 | 570 | 8.8 |
| 48 | toluene | 62 | 500 | 8.1 |
| 49 | motor oil (20W-50) | 56 | 547 | 9.8 |

As can be seen from the data in Table 15, the cylinders containing the microfiber microwebs are excellent sorbent materials for a broad range of both aqueous and organic liquids.

EXAMPLE 50 AND COMPARATIVE EXAMPLES C11–C14

For Example 50, a microfiber microweb-containing cylinder was prepared as in Examples 43–49, except that the cylinder was about 8 cm in diameter and 125 cm long. The cylinder was placed in a pan of water for five minutes and then allowed to drain for two minutes. The weight of the dry microfiber microweb-containing cylinder, the weight of the water sorbed, and the weight ratio of the water sorbed to the weight of the dry cylinder are reported in Table 16. For Comparative Examples C11–C13, commercially available cylinders, similar in size to the cylinder of Example 50, containing highly milled polypropylene fibers about 10 microns in diameter and about 100–200 microns in length, ground corn cobs, and wood pulp, respectively, were tested as in Example 50. For Comparative Example 14, a rolled cylinder of blown polypropylene microfiber sheet material, similar in size to Example 50, was tested as in Example 50. The test results are set forth in Table 16.

TABLE 16

| Example | Cylinder weight (g) | Sorbed water (g) | Weight ratio water/cylinder |
|---|---|---|---|
| 50 | 350 | 3050 | 8.7 |
| C11 | 500 | 2425 | 4.9 |
| C12 | 500 | 1525 | 2.8 |
| C13 | 325 | 2825 | 8.7 |
| C14 | 200 | 1550 | 7.8 |

From the data in Table 16, it can be seen that the cylinder of Example 50 provided greater sorbency of the water than did any of the comparative cylinders except the wood pulp containing cylinder of Comparative Example C13. Various modifications and alterations of this invention will be apparent to those skilled in the art without departing from the scope and spirit of this invention and this invention should not be restricted to that set forth herein for illustrative purposes.

What is claimed is:

1. Microfiber microwebs comprising relatively dense microfiber nuclei with individual fibers and/or fiber bundles protruding therefrom.

2. The microfiber microwebs of claim 1 wherein said nuclei have an average diameter of about 0.05 to 4 mm.

3. The microfiber microwebs of claim 1 wherein said fibers and/or fiber bundles extend from said nucleus to provide said microweb with a total diameter of about 0.07 to 10 mm.

4. The microfiber microwebs of claim 1 further comprising particulate material.

5. The microfiber microweb of claim 4 wherein said particulate material is sorbent particulate material.

6. A nonwoven web comprising carrier fibers and microfiber microwebs dispersed among the carrier fibers according to claim 1.

7. The nonwoven web of claim 6 wherein said carrier fibers are blown fibers.

8. The nonwoven web of claim 7 wherein said blown fibers are melt blown microfibers.

9. The nonwoven web of claim 8 wherein said nonwoven web further contains staple fibers.

10. The nonwoven web of claim 9 wherein said staple fibers are crimped bulking fibers.

11. The nonwoven web of claim 7 wherein said microwebs further contain sorbent particulate material.

12. The nonwoven web of claim 6 wherein said carrier fibers are air-laid staple fibers.

13. The nonwoven web of claim 6 wherein said carrier fibers are wood pulp fibers.

14. A sorbent article comprising a nonwoven web comprising carrier fibers and microfiber microwebs according to claim 1.

15. A disposable diaper comprising a nonwoven web comprising carrier fibers and microfiber microwebs according to claim 1.

16. A catamenial device comprising a nonwoven web comprising carrier fibers and microfiber microwebs according to claim 1.

17. An incontinent device comprising a nonwoven web comprising carrier fibers and microfiber microwebs according to claim 1.

18. A surgical dressing comprising a nonwoven web comprising carrier fibers and microfiber microwebs according to claim 1.

19. A shaped article comprising a porous covering material having contained therein microfiber microwebs according to claim 1.

20. Sorbent materials comprising carrier fibers and microfiber microwebs dispersed among said carrier fibers according to claim 1.

21. Sorbent materials of claim 20 further comprising particulate material.

22. Filtration media comprising carrier fibers and microfiber microwebs dispersed among said carrier fibers according to claim 1.

23. Thermal insulation comprising carrier fibers microfiber microwebs dispersed among said carrier fibers according to claim 1.

* * * * *

UNITED STATES PATENT AND TRADEMARK OFFICE
CERTIFICATE OF CORRECTION

PATENT NO. : 4,813,948
DATED : March 21, 1989
INVENTOR(S) : THOMAS I. INSLEY

It is certified that error appears in the above-identified patent and that said Letters Patent is hereby corrected as shown below:

Col. 24, line 33, Claim 23. Insert "and" after fibers.
Col. 1, line 41, "were" should be -- where -- .
Col. 13, line 20, "$\mu\Omega^{31}{}^{1}\cdot cm^{-1}$" should be -- $\mu\Omega^{-1}\cdot cm^{-1}$ -- .

Signed and Sealed this

Eleventh Day of June, 1991

Attest:

HARRY F. MANBECK, JR.

*Attesting Officer*  *Commissioner of Patents and Trademarks*